US008324417B2

(12) United States Patent
Hart et al.

(10) Patent No.: US 8,324,417 B2
(45) Date of Patent: Dec. 4, 2012

(54) PROCESS FOR THE PREPARATION OF (S)-2-AMINO-5-CYCLOPROPYL-4,4-DIFLUOROPENTANOIC ACID AND ALKYL ESTERS AND ACID SALTS THEREOF

(75) Inventors: Barry Hart, Palo Alto, CA (US); Jeff Dener, Millbrae, CA (US); Michael Green, Half Moon Bay, CA (US); Michael Standen, Albany, OR (US); Oldrich Kocian, Camelford (GB)

(73) Assignee: ViroBay, Inc., Menlo Park, CA (US)

( * ) Notice: Subject to any disclaimer, the term of this patent is extended or adjusted under 35 U.S.C. 154(b) by 70 days.

(21) Appl. No.: 12/857,477

(22) Filed: Aug. 16, 2010

(65) Prior Publication Data

US 2011/0046406 A1    Feb. 24, 2011

Related U.S. Application Data

(60) Provisional application No. 61/235,075, filed on Aug. 19, 2009.

(51) Int. Cl.
C07C 213/02    (2006.01)
C07C 303/26    (2006.01)
C07C 67/303    (2006.01)
C07C 67/307    (2006.01)

(52) U.S. Cl. .................. 558/54; 560/124; 562/506

(58) Field of Classification Search ............... None
See application file for complete search history.

(56) References Cited

U.S. PATENT DOCUMENTS

| | | | |
|---|---|---|---|
| 6,420,364 B1 | 7/2002 | Emmanuel et al. | |
| 6,506,733 B1 | 1/2003 | Buysse et al. | |
| 6,610,692 B1 * | 8/2003 | Sanderson et al. | 514/248 |
| 6,730,671 B2 | 5/2004 | Cywin et al. | |
| 7,312,211 B2 | 12/2007 | Bekkali et al. | |
| 7,781,487 B2 * | 8/2010 | Link et al. | 514/646 |
| 7,893,112 B2 * | 2/2011 | Link et al. | 514/620 |
| 2003/0092634 A1 | 5/2003 | Buysse et al. | |
| 2003/0232863 A1 | 12/2003 | Bayly et al. | |
| 2004/0127426 A1 | 7/2004 | Graupe et al. | |
| 2005/0014941 A1 | 1/2005 | Black et al. | |
| 2005/0182096 A1 | 8/2005 | Link et al. | |
| 2005/0240023 A1 | 10/2005 | Bayly et al. | |
| 2006/0111440 A1 | 5/2006 | Gauthier et al. | |
| 2006/0189657 A1 | 8/2006 | Thurairatnam et al. | |
| 2006/0287402 A1 | 12/2006 | Bayly et al. | |
| 2008/0214676 A1 * | 9/2008 | Link et al. | 514/646 |
| 2008/0293819 A1 * | 11/2008 | Link et al. | 514/620 |

FOREIGN PATENT DOCUMENTS

| | | |
|---|---|---|
| EP | 0623627 A1 | 9/1994 |
| JP | 2004-123556 * | 4/2004 |
| WO | WO 99/24460 A3 | 5/1999 |
| WO | WO 00/09543 A2 | 2/2000 |
| WO | WO00-26211 * | 5/2000 |
| WO | WO 00/51998 A1 | 9/2000 |
| WO | WO 00/55125 A2 | 9/2000 |
| WO | WO 00/55144 A1 | 9/2000 |
| WO | WO 01/19796 A1 | 3/2001 |
| WO | WO 01/19816 A1 | 3/2001 |
| WO | WO 01/49288 A1 | 7/2001 |
| WO | WO 01/68645 A2 | 9/2001 |
| WO | WO 02/20485 A1 | 3/2002 |
| WO | WO 02/26211 A1 | 4/2002 |
| WO | WO 02/069901 A2 | 9/2002 |
| WO | WO 02/074904 A2 | 9/2002 |
| WO | WO 02/098850 A2 | 12/2002 |
| WO | WO 03/024924 A1 | 3/2003 |
| WO | WO 03/029200 A2 | 4/2003 |
| WO | WO 03/075836 A2 | 9/2003 |
| WO | WO 03/097617 A1 | 11/2003 |
| WO | WO 2004/083182 A1 | 3/2004 |
| WO | WO 2004/103996 A1 | 12/2004 |
| WO | WO 2004/108661 A1 | 12/2004 |
| WO | WO 2005/002454 A1 | 3/2005 |
| WO | WO 2005/021487 A1 | 3/2005 |
| WO | WO 2005/028429 A2 | 3/2005 |
| WO | WO 2005/035525 A2 | 4/2005 |
| WO | WO 2005/040142 A1 | 5/2005 |
| WO | WO 2005/058348 A1 | 6/2005 |
| WO | WO 2005/063742 A2 | 7/2005 |
| WO | WO 2005/074904 A2 | 8/2005 |
| WO | WO 2006/034004 A2 | 3/2006 |
| WO | WO 2008/042968 A2 | 4/2008 |

OTHER PUBLICATIONS

Bundgaard, et al. "A Novel Solution-Stable, Water-Soluble Prodrug Type for Drugs Containing a Hydroxyl or an NH-Acidic Group," J. Med. Chem., 1989, vol. 32, No. 12, pp. 2503-2507.

Gong, Y. et al. "Convenient Substitution of Hydroxypyridines with Trifluoroacetaldehyde Ethyl Hemiacetal," Journal of Heterocyclic Chemistry 2001, vol. 38, No. 1, pp. 25-28.

Greenspan, et al. "Identification of Dipeptidyl Nitriles as Potent and Selective Inhibitors of Cathepsin B through Structure-Based Drug Design," J. Med. Chem., 2001, vol. 44, pp. 4524-4534.

Volonterio, et al. "Solution/solid-phase synthesis of partially modified retro-ψ [NHCH(CF$_3$)]-peptidyl hydroxamates," Tetrahedron Letters, 2001, vol. 42, pp. 3141-3144.

* cited by examiner

*Primary Examiner* — Fiona T Powers
(74) *Attorney, Agent, or Firm* — Kilpatrick Townsend & Stockton LLP

(57) ABSTRACT

The present invention relates to a process for the preparation of alkyl esters of (S)-2-amino-5-cyclopropyl-4,4-difluoropentanoic acid, which are intermediates useful in the synthesis of (S)—N-(1-cyanocyclopropyl)-5-cyclopropyl-4,4-difluoro-2-((S)-2,2,2-trifluoro-1-(4-fluorophenyl)ethylamino) pentanamide and related compounds, which are compounds that are cysteine protease inhibitors.

11 Claims, 6 Drawing Sheets

Results processed by 200 nm

| | Peak Name | Retention Time | Peak Area | % Peak Area |
|---|---|---|---|---|
| 1 | D-Isomer | 8.300 | | |
| 2 | L-Isomer | 9.801 | 2867844 | 100.00 |

PROCESS FOR THE PREPARATION OF (S)-2-AMINO-5-CYCLOPROPYL-4,4-DIFLUOROPENTANOIC ACID AND ALKYL ESTERS AND ACID SALTS THEREOF

CROSS-REFERENCES TO RELATED APPLICATIONS

This application claims priority to U.S. Provisional Patent Application No. 61/235,075, filed Aug. 19, 2009, which is herein incorporated by reference in its entirety for all purpose.

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

The present invention relates to a process for the preparation of alkyl esters of (S) 2-amino-5-cyclopropyl-4,4-difluoropentanoic acid, which are intermediates useful in the synthesis of (S)—N-(1-cyanocyclopropyl)-5-cyclopropyl-4,4-difluoro-2-((S)-2,2,2-trifluoro-1-(4-fluorophenyl) ethylamino)pentanamide and related compounds, which are compounds that are cysteine protease inhibitors. In particular, the process is suitable for large scale synthesis of (S)-methyl 2-amino-5-cyclopropyl-4,4-difluoropentanoate or (S)-ethyl 2-amino-5-cyclopropyl-4,4-difluoropentanoate.

BACKGROUND

Cysteine proteases represent a class of peptidases characterized by the presence of a cysteine residue in the catalytic site of the enzyme. Cysteine proteases are associated with the normal degradation and processing of proteins. However, abnormal activity of cysteine proteases, e.g., as a result of increased expression or enhanced activation, has been shown to have pathological consequences. Examples of cysteine proteases are cathepsins B, K, L, and S.

In particular, the normal protease activity of cathepsin S or its increased expression and activity are associated with a wide range of disease states. In particular, cathepsin S is implicated in Alzheimer's disease, and in certain autoimmune disorders, including, but not limited to juvenile onset diabetes, multiple sclerosis, psoriasis, inflammatory bowel disease, pemphigus vulgaris, Graves' disease, myasthenia gravis, systemic lupus erythemotasus, rheumatoid arthritis, neuropathic pain, and Hashimoto's thyroiditis. In addition, cathepsin S is implicated in: allergic disorders, including, but not limited to, asthma; and allogenic immune responses, including, but not limited to, rejection of organ transplants or tissue grafts, or immune response to therapeutic agents. Altered expression or activity of cathepsin S has also been implicated in atherosclerosis and the rupture of atherosclerotic plaque.

In view of the number of diseases or conditions related to the activity or the increased expression of cathepsin S, compounds that are capable of inhibiting such activity or expression would accordingly be useful as therapeutic agents for the treatment of certain autoimmune disorders, neuropathic pain, Alzheimer's disease, and atherosclerosis.

In U.S. Patent Application 2008/0214676, and U.S. patent application Ser. No. 12/060,774, the complete disclosures of which is hereby incorporated by reference, a series of compounds useful as cathepsin S inhibitors were disclosed. One of those compounds, (S)—N-(1-cyanocyclopropyl)-5-cyclopropyl-4,4-difluoro-2-((S)-2,2,2-trifluoro-1-(4-fluorophenyl)ethylamino)pentanamide, has been chosen for further study as a clinical candidate for the treatment of conditions related to the activity or the increased expression of cathepsin S. Accordingly, an efficient method of preparing this compound on a large scale is desired, particularly a method of preparing the final intermediate, (S)-methyl 2-amino-5-cyclopropyl-4,4-difluoropentanoate or (5)-ethyl 2-amino-5-cyclopropyl-4,4-difluoropentanoate.

SUMMARY OF THE INVENTION

One aspect of this invention is a process for the preparation of a (S)-alkyl 5-cyclopropyl-4,4-difluoropentanoate of Formula 1:

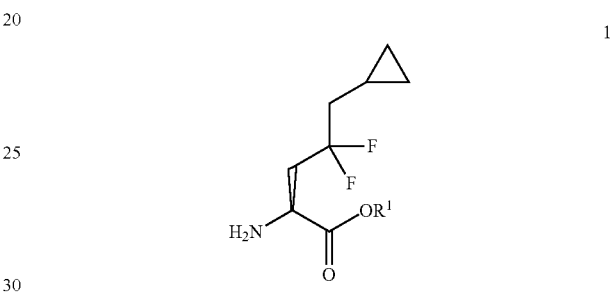

or a salt thereof, where $R^1$ is a primary or secondary alkyl having 1 to 5 carbon atoms, which process comprises:

(a) selectively hydrolyzing a compound of Formula 2:

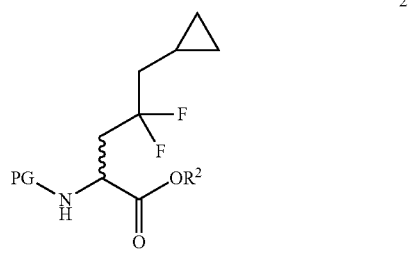

where PG is an amino protecting group and $R^2$ is alkyl, cycloalkyl, cycloalkylalkyl or arylalkyl, wherein any alkyl group comprising $R^2$ is a primary or secondary alkyl having 1 to 5 carbon atoms, to give a mixture of protected (R)-2-amino-5-cyclopropyl-4,4-difluoropentanoate and protected (S)-2-amino-5-cyclopropyl-4,4-difluoropentanoic acid;

(b) isolating the protected (S)-2-amino-5-cyclopropyl-4,4-difluoropentanoic acid;

(c) deprotecting the protected (5)-2-(amino)-5-cyclopropyl-4,4-difluoropentanoic acid to give (S)-2-amino-5-cyclopropyl-4,4-difluoropentanoic acid;

(d) treating the (S)-2-amino-5-cyclopropyl-4,4-difluoropentanoic acid with alcohol $R^1OH$; and (e) optionally converting the free base of the compound of Formula I to the acid addition salt.

A second aspect of this invention is a process for the preparation of a compound of Formula 2:

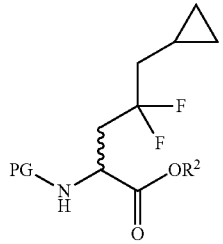

where PG is a protecting group and $R^2$ is alkyl, cycloalkyl, cycloalkylalkyl or arylalkyl, wherein any alkyl group comprising $R^2$ is a primary or secondary alkyl having 1 to 5 carbon atoms, which process comprises:

(a) condensing the 3-cyclopropyl-2,2-difluoropropyl perfluorobutane-1-sulfonate of Formula 4:

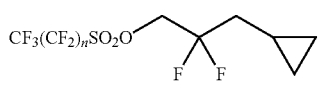

where n is 0, 1, 2, 3 or 4, with a 2-(diphenylmethyleneamino) acetate anion of Formula 3:

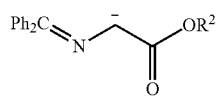

where $R^2$ is alkyl, cycloalkyl, cycloalkylalkyl or arylalkyl, wherein any alkyl group comprising $R^2$ is a primary or secondary alkyl having 1 to 5 carbon atoms, to give the corresponding (R,S)-2-(diphenylmethyleneamino)-5-cyclopropyl-4,4-difluoropentanoate;

(b) hydrolyzing the (R,S)-2-(diphenylmethyleneamino)-5-cyclopropyl-4,4-difluoropentanoate with acid to give the corresponding (R,S)-2-amino-5-cyclopropyl-4,4-difluoropentanoate, (c) optionally treating the (R,S)-2-amino-5-cyclopropyl-4,4-difluoropentanoate with acid to give the corresponding (R,S)-2-amino-5-cyclopropyl-4,4-difluoropentanoate acid addition salt; and (d) treating the (R,S)-2-amino-5-cyclopropyl-4,4-difluoropentanoate or salt thereof with an amino protecting agent.

A third aspect of this invention is a process for the preparation of a compound of Formula 4:

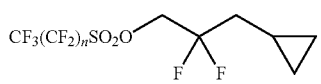

where n is 0, 1, 2, 3 or 4, which process comprises (a) reducing the alkyl 3-cyclopropyl-2,2-difluoropropanoate of Formula 5:

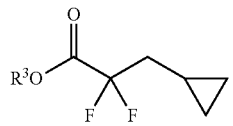

where $R^3$ is hydrogen or alkyl having 1 to 5 carbon atoms, to give 3-cyclopropyl-2,2-difluoropropan-1-ol and (b) reacting the 3-cyclopropyl-2,2-difluoropropan-1-ol with a perfluoroalkyl sulfonyl halide or a perfluoroalkyl sulfonic anhydride having the formula $CF_3(CF_2)_nSO_2X$ or $(CF_3(CF_2)_nSO_2)_2O$, respectively, where n is 0, 1, 2, 3 or 4 and X is chloro or fluoro.

A fourth aspect of this invention is a process for the preparation of ethyl 3-cyclopropyl-2,2-difluoropropanoate, which process comprises reacting ethyl 2,2-difluoropent-4-enoate with diiodomethane in the presence of a strong acid and diethylzinc or a zinc/copper couple.

A fifth aspect of this invention is a process for the preparation of ethyl 3-cyclopropyl-2,2-difluoropropanoate, which process comprises: (a) reacting bromomethylcyclopropane with 2-carboethoxy-1,3-dithiane in the presence of strong base to give ethyl 2-(cyclopropylmethyl)-1,3-dithiane-2-carboxylate; (b) reacting the ethyl 2-(cyclopropylmethyl)-1,3-dithiane-2-carboxylate with N-bromosuccinimide to give ethyl 3-cyclopropyl-2-oxopropanoate; and (c) reacting the ethyl 3-cyclopropyl-2-oxopropanoate with a fluorinating agent.

DETAILED DESCRIPTION OF THE INVENTION

Figure 1:
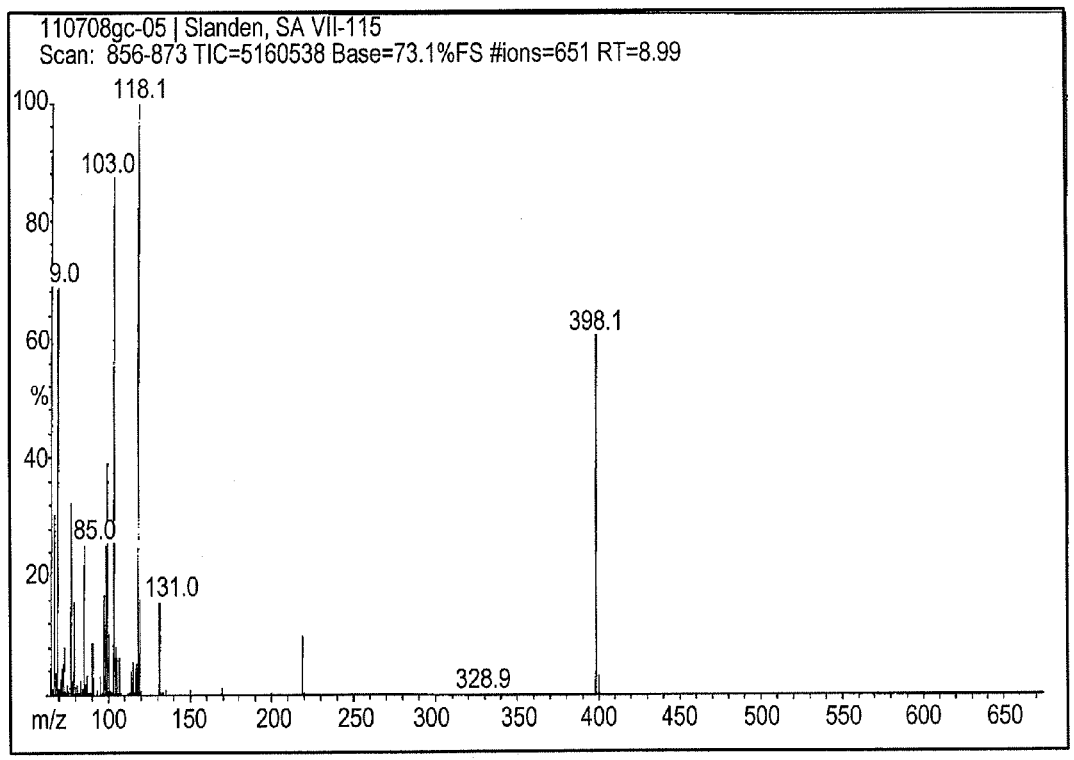
FIG. 1 shows the gas chromatograph-mass spectrum (GC-MS) of 3-Cyclopropyl-2,2-difluoropropyl 1,1,2,2,3,3,4,4,4-nonafluorobutane-1-sulfonate as described in Example 7.
Figure 2:
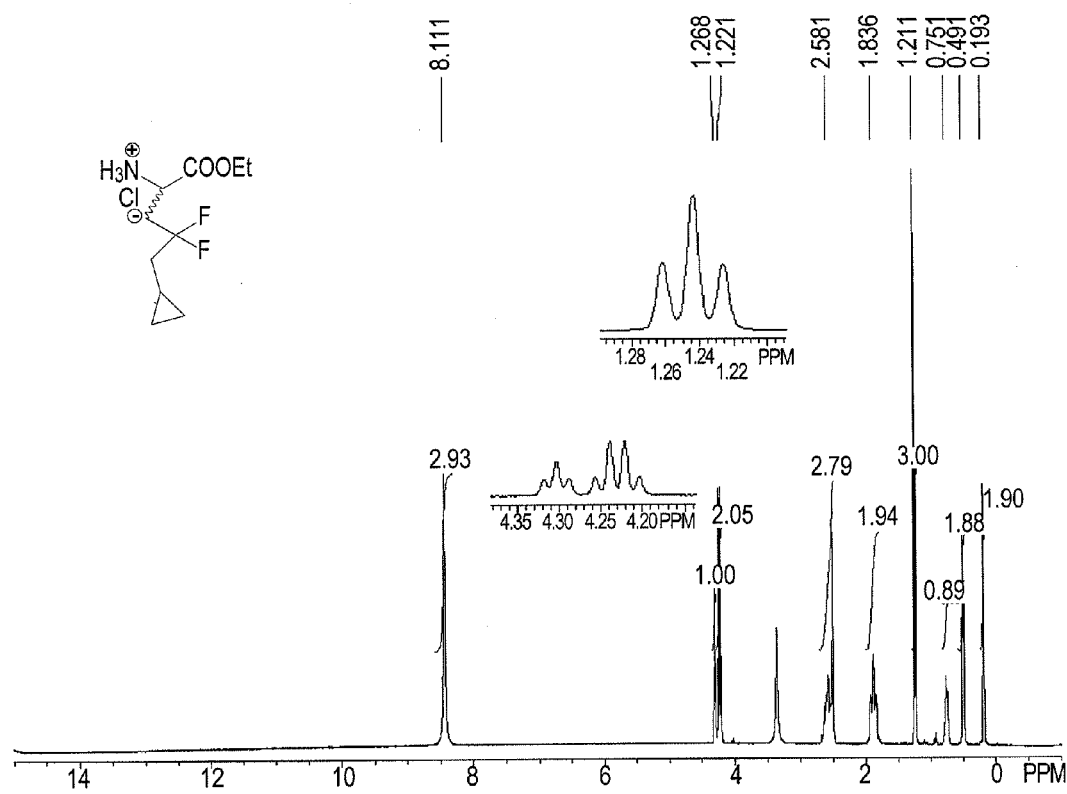
FIG. 2 illustrates the proton NMR spectrum of ethyl(R,S)-2-amino-5-cyclopropyl-4,4-difluoropentanoate hydrochloride as described in Example 8.
Figure 3:
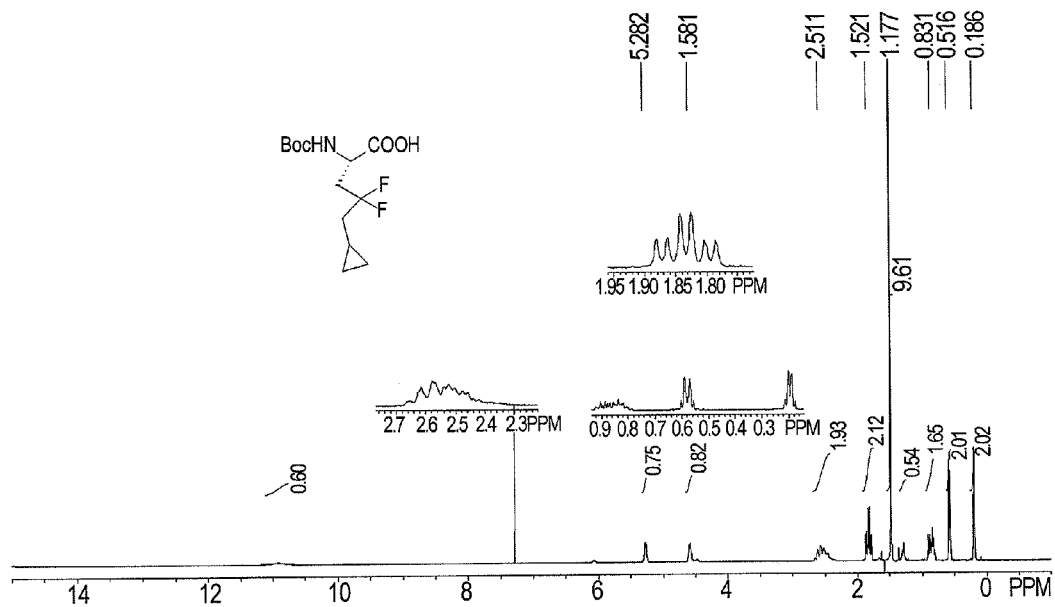
FIG. 3 illustrates the proton NMR spectrum of (S)-2-(tert-Butoxycarbonylamino)-5-cyclopropyl-4,4-difluoropentanoic acid as described in Example 10.
Figure 4:
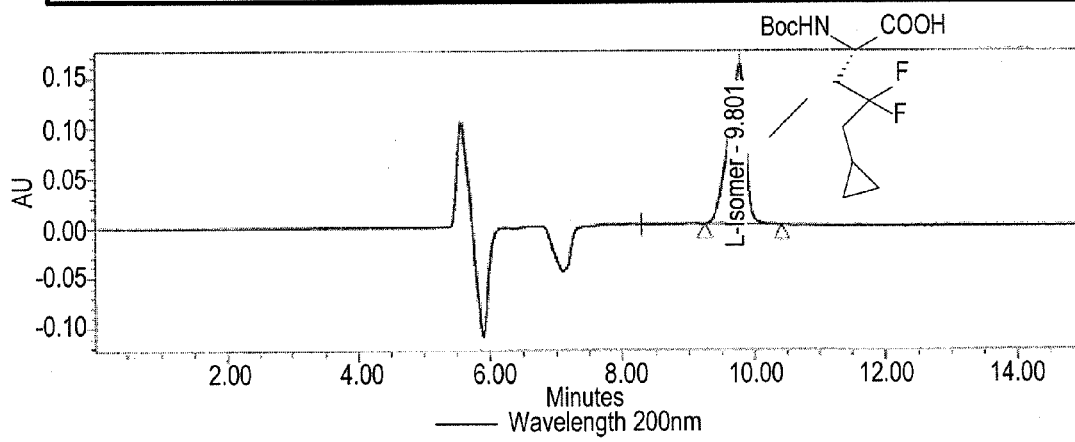
FIG. 4 illustrates the chiral HPLC profile of (S)-2-(tert-Butoxycarbonylamino)-5-cyclopropyl-4,4-difluoropentanoic acid as described in Example 10.
Figure 5:
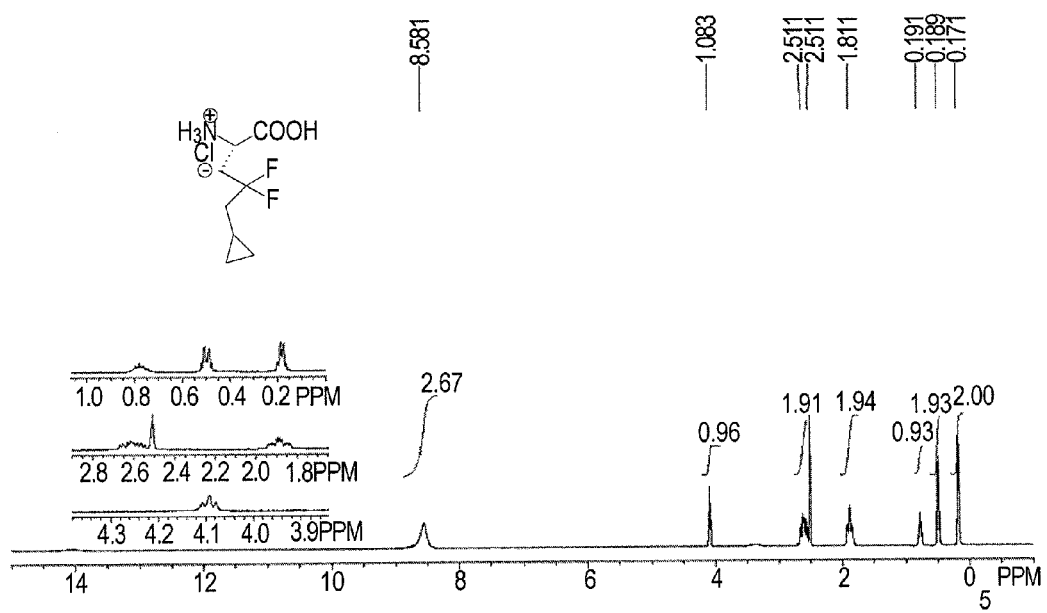
FIG. 5 illustrates the proton NMR spectrum of (S)-2-Amino-5-cyclopropyl-4,4-difluoropentanoic acid hydrochloride as described in Example 11.
Figure 6:
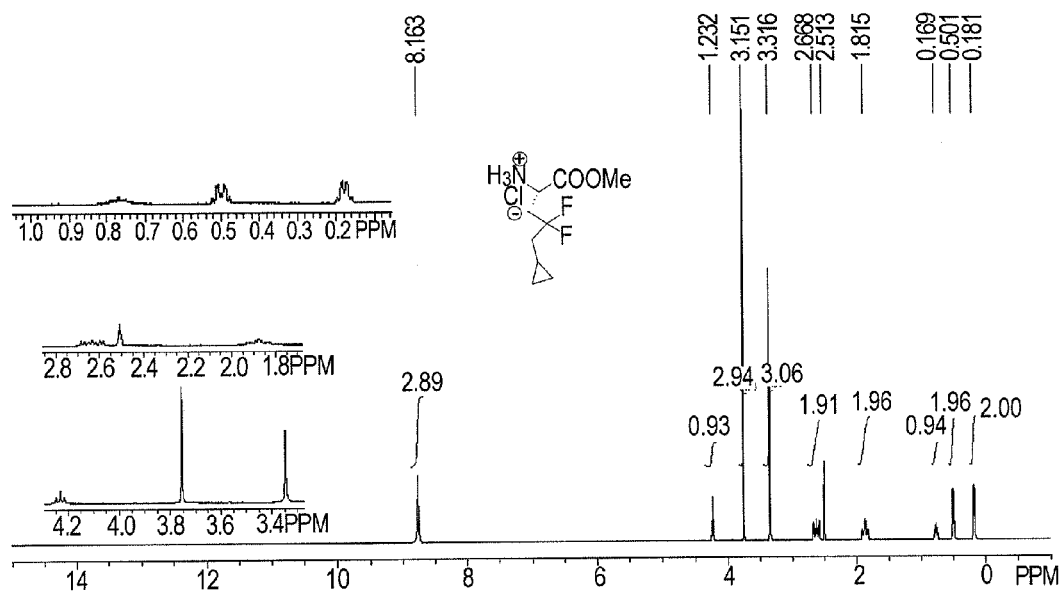
FIG. 6 illustrates the proton NMR spectrum of methyl 2-amino-5-cyclopropyl-4,4-difluoropentanoate hydrochloride as described in Example 12.

The present invention provides processes for the preparation of 2-amino-5-cyclopropyl-4,4-difluoropentanoic acid, and alkyl esters thereof, and acid salts of the acid or esters. Such compounds are key intermediates in the production of cathepsin S inhibitors. In U.S. Patent Application 2008/0214676, this intermediate is prepared by (a) converting an amino protected derivative of 2-amino-3-iodopropanoic acid to the corresponding amino protected 2-amino-5-cyclopropyl-4-oxopentanoic acid; (b) converting the amino protected 2-amino-5-cyclopropyl-4-oxopentanoic acid to the corresponding amino protected 2-amino-5-cyclopropyl-4,4-difluoropentanoic acid; and then (c) deprotecting to afford the 2-amino-5-cyclopropyl-4,4-difluoropentanoic acid.

Although this procedure is a convenient method of preparing intermediates for the compounds of the invention on a small scale, it is not suitable for large scale preparations. It is difficult to scale up due to the heterogeneous nature of the reactions involved, and it is not reliably reproducible. Also, the conversion of a carbonyl group to a difluoro moiety gives a complex mixture, which is difficult to purify on a large scale. Accordingly, it is desired to provide convenient methods of preparing (S)-methyl 2-amino-5-cyclopropyl-4,4-difluoropentanoate on a large scale.

DEFINITIONS

Unless otherwise stated, the following terms used in the specification and claims are defined for the purposes of this Application and have the following meanings.

"Alkyl" represented by itself means a straight or branched, saturated or unsaturated, aliphatic univalent radical having the number of carbon atoms indicated, e.g., alky having 1 to 5 carbon atoms includes methyl, ethyl, n-propyl, isopropyl, n-butyl, sec-butyl, but-3-enyl, isobutyl and the like. Alkyl represented along with another radical (e.g., as in arylalkyl or cycloalkylalkyl) means alkyl as defined herein, but wherein the alkyl is substituted with another radical, e.g., aryl or cycloalkyl.

"Amino protecting group" means any group which the amino group to which it is attached is blocked from reaction and can be easily removed, e.g., benzyloxycarbonyl, tert-butoxycarbonyl, and the like. Suitable amino protecting groups and methods for their removal can be found in T. W. Greene, Protective Groups in Organic Synthesis, 3$^{rd}$ edition, John Wiley & Sons, Inc. 1999.

"Aryl" means a univalent radical consisting of monocyclic or bicyclic ring assembly (fused or lined by a single bond) containing from 6 to 14 ring carbon atoms, wherein each ring is comprised of 6 ring atoms and is aromatic or when fused with a second ring forms an aromatic ring assembly, e.g., phenyl, naphthyl, biphenylyl, and the like.

"Cycloalkyl" means a univalent radical consisting of a saturated or partially unsaturated, monocyclic, bicyclic ring (fused or lined by a single bond) or bridged polycyclic ring assembly containing from 3 to 14 ring carbon atoms, e.g., cyclopropyl, cyclohexyl, bicycle[2.2.2]octanyl, and the like.

"Primary alkyl" means alkyl as defined herein, wherein the carbon atom serving as the point of attachment has all hydrogens attached to it, i.e., methyl, or hydrogens and one carbon atom of the remaining carbon atoms in the radical attached to it, e.g., ethyl, n-propyl, n-butyl, isobutyl, n-pentyl, 2-methylbutyl, and the like, and, when the alkyl of cycloalkylalkyl or arylalkyl is designated as primary alkyl, then cyclohexylmethyl, benzyl, phenethyl, 3-cyclopentylpropyl, and the like.

"Secondary alkyl" means alkyl as defined herein, wherein the carbon atom serving as the point of attachment has two carbon atoms of the remaining carbon atoms in the radical directly attached to it, e.g., isopropyl, sec-butyl, sec-pentyl, 1-methylbutyl, and the like, and, when the alkyl of cycloalkylalkyl or arylalkyl is designated as secondary alkyl, then 1-phenylethyl, 1-cyclobutylpropyl, and the like.

PREFERRED EMBODIMENTS

A preferred aspect of the invention is a process for the preparation of (S)-methyl 2-amino-5-cyclopropyl-4,4-difluoropentanoate hydrochloride, which process comprises: (a) reacting (R,S)-ethyl 2-(tert-butoxycarbonylamino)-5-cyclopropyl-4,4-difluoropentanoate with Alcalase to give a mixture of (R)-ethyl 2-(tert-butoxycarbonylamino)-5-cyclopropyl-4,4-difluoropentanoate and (S)-2-(tert-butoxycarbonylamino)-5-cyclopropyl-4,4-difluoropentanoic acid; (b) isolating the (S)-2-(tert-butoxycarbonylamino)-5-cyclopropyl-4,4-difluoropentanoic acid; (c) deprotecting the (S)-2-(tert-butoxycarbonylamino)-5-cyclopropyl-4,4-difluoropentanoic acid with hydrochloric acid to give (S)-2-amino-5-cyclopropyl-4,4-difluoropentanoic acid hydrochloride; and (d) treating the (S)-2-amino-5-cyclopropyl-4,4-difluoropentanoic acid hydrochloride with methanol.

A second preferred aspect of this invention is a process for the preparation of (R,S)-ethyl 2-(tert-butoxycarbonylamino)-5-cyclopropyl-4,4-difluoropentanoate, which process comprises: (a) reacting 3-cyclopropyl-2,2-difluoropropyl 1,1,2,2,3,3,4,4,4-nonafluorobutane-1-sulfonate with (diphenylmethyleneamino)(ethoxycarbonyl)methanide to give ethyl(R,S)-2-(diphenylmethyleneamino)-5-cyclopropyl-4,4-difluoropentanoate; (b) hydrolyzing the ethyl (R,S)-2-(diphenylmethyleneamino)-5-cyclopropyl-4,4-difluoropentanoate with acid to give ethyl(R,S)-2-amino-5-cyclopropyl-4,4-difluoropentanoate, (c) treating the ethyl(R,S)-2-amino-5-cyclopropyl-4,4-difluoropentanoate with hydrochloric acid to give ethyl(R,S)-2-amino-5-cyclopropyl-4,4-difluoropentanoate hydrochloride; and (d) treating the ethyl(R,S)-2-amino-5-cyclopropyl-4,4-difluoropentanoate hydrochloride with di-tert-butyldicarbonate.

A third preferred aspect of this invention is a process for the preparation of 3-cyclopropyl-2,2-difluoropropyl 1,1,2,2,3,3,4,4,4-nonafluorobutane-1-sulfonate, which process comprises: (a) reducing ethyl 3-cyclopropyl-2,2-difluoropropanoate to give 3-cyclopropyl-2,2-difluoropropan-1-ol and (b) reacting the 3-cyclopropyl-2,2-difluoropropan-1-ol with perfluorobutane sulfonyl fluoride.

A fourth preferred aspect of this invention is a process for the preparation of ethyl 3-cyclopropyl-2,2-difluoropropanoate, which process comprises reacting ethyl 2,2-difluoropent-4-enoate with diiodomethane and either diethylzinc or a zinc/copper couple in the presence of trifluoroacetic acid.

Chemistry:

The scale up preparation of (S)-alkyl 2-amino-5-cyclopropyl-4,4-difluoropentanoate or a salt thereof is set forth in the following Scheme 1:

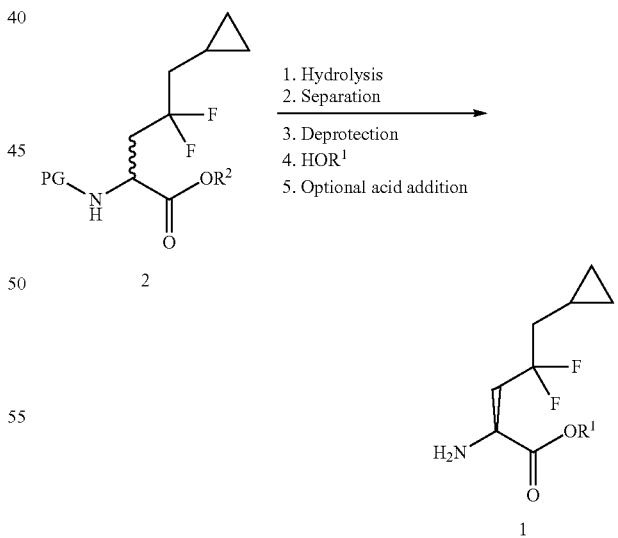

where PG is an amino protecting group, $R^1$ is a primary or secondary alkyl having 1 to 5 carbon atoms and $R^2$ is alkyl, cycloalkyl, cycloalkylalkyl or arylalkyl, wherein any alkyl group comprising $R^2$ is a primary or secondary alkyl having 1 to 5 carbon atoms.

The scale up preparation of (S)-alkyl 2-amino-5-cyclopropyl-4,4-difluoropentanoate or a salt thereof (Formula 1) comprises: (a) selectively hydrolyzing a compound of Formula 2 to give a mixture of protected (R)-2-amino-5-cyclopropyl-4,4-difluoropentanoate and protected (S)-2-amino-5-cyclopropyl-4,4-difluoropentanoic acid; (b) isolating the protected (S)-2-amino-5-cyclopropyl-4,4-difluoropentanoic acid; (c) deprotecting the protected (S)-2-(amino)-5-cyclopropyl-4,4-difluoropentanoic acid to give (S)-2-amino-5-cyclopropyl-4,4-difluoropentanoic acid; (d) treating the (S)-2-amino-5-cyclopropyl-4,4-difluoropentanoic acid with alcohol R$^1$OH; (e) and optionally converting the free base of the compound of Formula I to the acid addition salt.

The selective hydrolysis is carried out with an appropriate selective hydrolyzing agent in the presence of a mild base, e.g., sodium bicarbonate, in an inert solvent, e.g., a mixture of acetone and water, at a temperature of about 30° C. and requires 8 to 24 hours to complete. Suitable hydrolyzing agents are commercially available, e.g., Alcalase, α-Chymotrypsin, Ficin, Papain, Subtilisin Carlsberg (the major esterase component of Alcalase), *Aspergillus melleus* protease (Amano P), *Aspergillus niger* lipase, *Aspergillus oryzae* protease (Amano A), *Aspergillus Sojae* protease (Sigma Type XIX), Porcine pancreatic lipase, *Pseudomonas cepacia* lipase, *Rhizopus javanicus* lipase, *Rhizopus niveus* protease (Amano Newlase F), *Bacillus subtillis* protease, *Bacillus licheniformis* protease (Sigma Type VIII), Pronase, and Baker's yeast (*Saccharomuces cerevisiae*).

Isolation of the protected (S)-2-amino-5-cyclopropyl-4,4-difluoropentanoic acid is carried out by conventional means. For example, the unreacted amino-protected (R)-alkyl 2-amino-5-cyclopropyl-4,4-difluoropentanoate is first extracted from the mixture with a suitable organic solvent, e.g., methyl tert-butyl ether. The aqueous layer is then acidified to about pH 2 and the desired protected (S)-2-amino-5-cyclopropyl-4,4-difluoropentanoic acid is then extracted with a suitable organic solvent, e.g., methyl tert-butyl ether.

Deprotection can be effected by any means which removes the protective group and gives the desired product in reasonable yield. A detailed description of the techniques applicable to the creation of protective groups and their removal can be found in T. W. Greene, Protective Groups in Organic Synthesis, 3$^{rd}$ edition, John Wiley & Sons, Inc. 1999. For example, where PG is benzyloxycarbonylamino deprotection is carried out with hydrogen in the presence of a catalyst, e.g. palladium, in an inert solvent, e.g. tetrahydrofuran, or where PG is tert-butoxycarbonylamino deprotection is carried out with acid, e.g., hydrochloric acid, in an inert solvent, e.g., acetonitrile, at about ambient temperature and requires 2 to 3 hours to complete. Esterification is carried out by reacting with the alcohol in the presence of a suitable reagent, e.g., thionyl chloride, hydrogen chloride gas, methanesulfonic acid, p-toluenesulfonic acid, acetyl chloride, and the like, at about 45° C. and requires about 18 to about 24 hours to complete. A detailed description of the process of Scheme 1 is set forth in Examples 10, 11 and 12, infra., which produced 53 g (42% yield) of final product.

The compound of Formula 2 is prepared as set forth in the following reaction Scheme 2:

Scheme 2

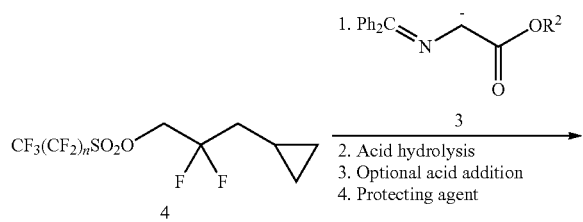

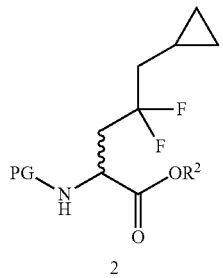

where n is 0, 1, 2, 3 or 4, PG is an amino protecting group and R$^2$ is alkyl, cycloalkyl, cycloalkylalkyl or arylalkyl, wherein any alkyl group comprising R$^2$ is a primary or secondary alkyl having 1 to 5 carbon atoms.

The compound of Formula 2 is prepared by (a) condensing 3-cyclopropyl-2,2-difluoropropyl perfluorobutane-1-sulfonate of Formula 4 with a 2-(diphenylmethyleneamino)acetate anion of Formula 3 to give the corresponding (R,S)-2-(diphenylmethyleneamino)-5-cyclopropyl-4,4-difluoropentanoate; (b) hydrolyzing the (R,S)-2-(diphenylmethyleneamino)-5-cyclopropyl-4,4-difluoropentanoate with acid to give the corresponding (R,S)-2-amino-5-cyclopropyl-4,4-difluoropentanoate (c) optionally treating the (R,S)-2-amino-5-cyclopropyl-4,4-difluoropentanoate with acid to give the corresponding (R,S)-2-amino-5-cyclopropyl-4,4-difluoropentanoate acid addition salt; and (d) treating the (R,S)-2-amino-5-cyclopropyl-4,4-difluoropentanoate or salt thereof with an amino protecting agent.

The condensation reaction is carried out by treating a corresponding 2-(diphenylmethyleneamino)acetate or 2-(benzhydrylimino)acetate with a strong non-nucleophilic base, e.g., potassium hexamethyldisilazane (KHMDS) or potassium tert-butoxide, to generate the 2-(diphenylmethyleneamino)acetate anion and then reacting the anion with the 3-cyclopropyl-2,2-difluoropropyl perfluoroalkane-1-sulfonate in a suitable solvent, e.g., tetrahydrofuran, at about ambient temperature and requires 12 to 24 hours to complete. The 3-cyclopropyl-2,2-difluoropropyl perfluoroalkanesulfonate is added slowly to a mixture of the 2-(diphenymethyleneamino)acetate anion and base at 0 to 30° C., after which the mixture is allowed to warm to ambient temperature. The hydrolysis step can be carried out with a strong acid, e.g., 25% sulfuric acid, and requires 2 to 3 hours to complete. The hydrochloride salt is formed by dissolving the amine in an inert solvent, e.g. tert-butyl methyl ether, adding gaseous hydrochloric acid and isolating the hydrochloride salt as a white solid.

The protection step is carried out under an inert atmosphere, e.g., nitrogen, in a suitable solvent, e.g., tetrahydrofuran, in the presence of a tertiary base, e.g, triethylamine, with an agent capable of protecting the amino group, e.g., di-tert-butyldicarbonate, at a temperature of about 10° C. and requires 1 to 5 hours to complete. The tertiary base is added slowly to the reaction mixture, maintaining the temperature below about 20° C. A detailed description of the process of Scheme 2 is set forth in Examples 8 and 9, infra. by which 55 g (72% yield) of final product was produced.

The 2-(benzhydrylimino)acetates are prepared by reacting benzhydrylamine with an appropriate glyoxylate hemiacetal. This reaction is carried out in a suitable solvent, e.g., methylene chloride, at about ambient temperature and requires 3 to 4 hours to complete.

The diphenylmethyleneaminoacetates are prepared by reacting benzophenone imine with an appropriate alkyl 2-aminoacetate hydrochloride. This reaction is carried out in a suitable solvent, e.g., methylene chloride, at about ambient temperature and requires 20 to 24 hours to complete.

3-Cyclopropyl-2,2-difluoropropyl perfluoroalkane-1-sulfonate is prepared as set forth in the following reaction Scheme 3:

Scheme 3

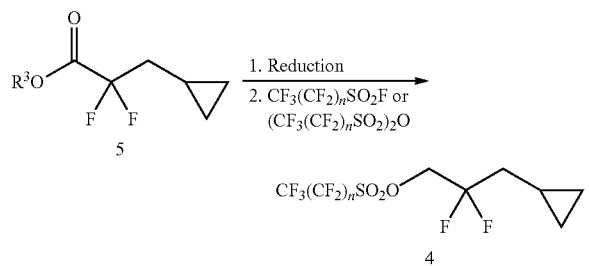

where n is 0, 1, 2, 3 or 4 and $R^3$ is hydrogen or alkyl having 1 to 5 carbon atoms.

The 3-cyclopropyl-2,2-difluoropropyl perfluoroalkane-1-sulfonate of Formula 4 is prepared by (a) reducing the alkyl 3-cyclopropyl-2,2-difluoropropanoate of Formula 5 to give 3-cyclopropyl-2,2-difluoropropan-1-ol and (b) reacting the 3-cyclopropyl-2,2-difluoropropan-1-ol with a perfluoroalkyl sulfonyl halide or a perfluorooalkyl sulfonic anhydride having the formula $CF_3(CF_2)_nSO_2X$ or $(CF_3(CF_2)_nSO_2)_2O$, respectively, where n is 0, 1, 2, 3 or 4 and X is chloro or fluoro, preferably perfluoroalkyl sulfonyl fluoride.

The reduction step is carried out in a suitable inert solvent, e.g., ethanol, in the presence of a suitable reducing agent, e.g., sodium borohydride at about 0° C. to ambient temperature and requires 10 to 24 hours to complete. The reaction with perfluoroalkylsulfonyl fluoride is carried out in an inert solvent, e.g., dichloromethane, in the presence of base, e.g., pyridine or triethylamine, at about ambient temperature and requires 1 to 2 hours to complete. The perfluoroalkylsulfonyl fluoride is added dropwise to the propanol and base mixture at 0° C. The reaction mixture is then allowed to warm to about ambient temperature. A detailed description of the process of Scheme 3 is set forth in Examples 4 and 7, infra., which produced 140 g (95% yield) of final product.

The alkyl 3-cyclopropyl-2,2-difluoropropanoate of Formula 4 is prepared as set forth in the following reaction Scheme 4:

Scheme 4

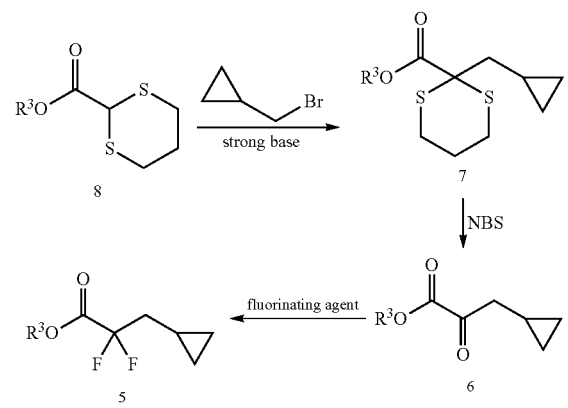

where $R^3$ is hydrogen or alkyl having 1 to 5 carbon atoms.

The alkyl 3-cyclopropyl-2,2-difluoropropanoate of Formula 5 is prepared by (a) reacting bromomethylcyclopropane with the 2-carboalkyloxy-1,3-dithiane of Formula 8 in the presence of strong base to give the corresponding alkyl 2-(cyclopropylmethyl)-1,3-dithiane-2-carboxylate of Formula 7; (b) reacting the alkyl 2-(cyclopropylmethyl)-1,3-dithiane-2-carboxylate with N-bromosuccinimide to give the corresponding alkyl 3-cyclopropyl-2-oxopropanoate of Formula 6; (c) reacting the alkyl 3-cyclopropyl-2-oxopropanoate with a fluorinating agent. Suitable fluorinating agents include bis(2-methoxyethyl)aminosulfur trifluoride (Deoxo-Fluor), diethylaminosulfur trifluoride (DAST), bromine trifluoride ($BrF_3$), 2,2-difluoro-1,3-dimethylimidazolidine (DFI), and the like; and (d) optionally hydrolysing the alkyl 3-cyclopropyl-2,2-difluoropropanoate with aqueous base to the alkyl 3-cyclopropyl-2,2-difluoropropanoic acid.

Preferably $R^3$ is methyl, ethyl or isopropyl. Most preferably $R^3$ is ethyl and the compound of Formula 5 is prepared by (a) reacting bromomethylcyclopropane with 2-carboethoxy-1,3-dithiane in the presence of a strong base to give ethyl 2-(cyclopropylmethyl)-1,3-dithiane-2-carboxylate; (b) reacting the ethyl 2-(cyclopropylmethyl)-1,3-dithiane-2-carboxylate with N-bromosuccinimide to give ethyl 3-cyclopropyl-2-oxopropanoate; and (c) reacting the ethyl 3-cyclopropyl-2-oxopropanoate with bis(2-methoxyethyl)aminosulfur trifluoride.

The reaction with the dithiane is carried out in a suitable solvent, e.g., N,N-dimethylformamide in the presence of a strong base, e.g., sodium hydride, at ambient temperature and requires 12 to 24 hours to complete. The dithiane is added slowly to a mixture of the bromomethylcyclopropane and base and the mixture is allowed to warm to ambient temperature. The reaction with the NBS is carried out a suitable solvent, e.g., acetone/water mixture at about −5° C. and requires about 1 hour to complete. The reaction with the fluorinating agent is carried out under an inert atmosphere, e.g., nitrogen, in a suitable solvent, e.g., methylene chloride, in the presence of a catalytic amount of ethanol and at room temperature and requires 10 to 24 hours to complete. The trifluoride was added slowly to a solution of the ethyl 3-cyclopropyl-2-oxopropanoate at −10° C. to 0° C., followed by addition of the ethanol. A detailed description of the process of Scheme 4 is set forth in Example 3, infra.

Alternatively, the alkyl 3-cyclopropyl-2,2-difluoropropanoate of Formula 4 is prepared as set forth in reaction Scheme 5:

Scheme 5

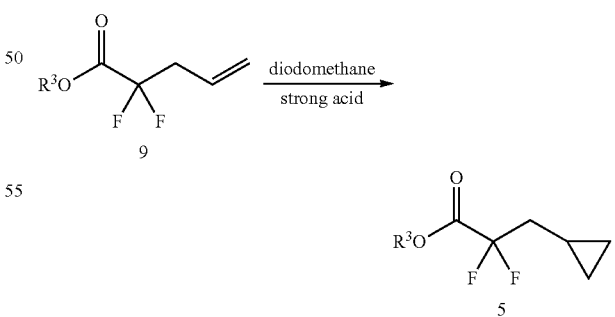

where $R^3$ is hydrogen or alkyl having 1 to 5 carbon atoms.

The alkyl 3-cyclopropyl-2,2-difluoropropanoate of Formula 5 is prepared by reacting the corresponding alkyl 2,2-difluoropent-4-enoate with diiodomethane in the presence of diethylzinc or zinc/copper couple. Preferably $R^3$ methyl, ethyl or isopropyl. Most preferably $R^3$ is ethyl and the compound of Formula 5 is prepared by reacting the corresponding ethyl 2,2-difluoropent-4-enoate with diiodomethane and diethylzinc or zinc/copper couple. This reaction is carried out in a suitable solvent, e.g., methylene chloride, in the presence of a strong acid, e.g., difluoroacetic acid, 2,2,3,3,3-pentafluoropropanoic acid, 2,2,3,3,4,4,4-heptafluorobutyric acid, trichloroacetic acid, dichloroacetic acid, dichlorofluoroacetic acid, trifluoroacetic acid, and the like at about reflux temperature and requires 18 to 24 hours to complete. The alkyl 3-cyclopropyl-2,2-difluoropropanoate optionally can be hydrolysed with aqueous base to the alkyl 3-cyclopropyl-2,2-difluoropropanoic acid. A detailed description of the process of Scheme 5 is set forth in Examples 1 and 2, infra.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Ethyl 3-cyclopropyl-2,2-difluoropropanoate

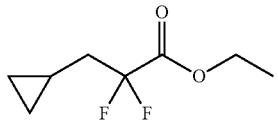

A solution of diethyl zinc (500 mL, 1.0 M in hexanes) in methylene chloride (700 mL) was chilled to −10° C. under nitrogen in a cooling bath. A solution of trifluoroacetic acid (57 g, 0.5 mol) in methylene chloride (50 mL) was added dropwise over 1 hour 45 minutes. The mixture was stirred for 30 minutes at −5° C. A solution of diiodomethane (133.9 g, 0.5 mol) in methylene chloride (50 mL) was added to the mixture over a period of 20 minutes. The mixture became homogenous upon stirring for 30 minutes at 0° C. A solution of ethyl 2,2-difluoropent-4-enoate (40 g, 0.244 mol) in methylene chloride (50 mL) was added dropwise over a period of 25 minutes and the cooling bath was removed. The mixture was stirred for 1 hour at room temperature and then for 15 hours at reflux. The reaction was quenched by addition of saturated aqueous ammonium chloride (500 mL) and stirring for 30 minutes. The biphasic mixture was poured into 500 mL of saturated aqueous ammonium chloride and the organic layer was separated. The aqueous layer was extracted with methylene chloride (3×300 mL) and the combined organic extracts were dried over magnesium sulfate and filtered. The solvent was removed from the filtrate under reduced pressure to afford ethyl 3-cyclopropyl-2,2-difluoropropanoate (43.5 g, quant), as light yellow oil, which was used in the Example 4 without further purification. $^1$H-NMR (400 MHz, CDCl$_3$): δ=0.12-0.22 (m, 2H), 0.49-0.59 (m, 2H), 0.75-0.91 (m, 1H), 1.37 (t, J=8 Hz, 3H), 1.95-2.05 (m, 2H), 4.34 (q, J=8 Hz, 2H).

Example 2

Ethyl 3-cyclopropyl-2,2-difluoropropanoate

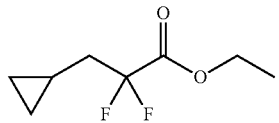

Zinc-copper (Zn—Cu) couple (1.6 Kg, 800 mol %) and dichloromethane (7.5 L) was charged into a dry 20.0 L, 4-neck round bottomed flask, fitted with an over head stirrer, a thermo socket and a condenser under a nitrogen atmosphere. Trifluoroacetic acid (235 mL, 100 mol %) was added to the above Zn—Cu couple at ambient temperature via addition funnel over 30 minutes. Diiodomethane (860 mL; 2.86 Kg; 10.7 mol; 352 mol %) was added to above the Zn—Cu couple at ambient temperature via addition funnel over 1.5 hours. The reaction temperature was raised to reflux and then ethyl 2,2-difluoropent-4-enoate (500 g; 3.05 mol) in dichloromethane (500 mL) was added slowly via addition funnel over 30 minutes at reflux. The reaction temperature was maintained for 40-60 hours at reflux. Progress of the reaction was monitored by GC analysis which showed about 93% conversion to product based on relative area % of the peaks corresponding to product and starting material. The reaction mass was cooled to 0-5° C. and 5% dilute hydrochloric acid (500 mL) was added then the solution was filtered and washed with dichloromethane (1500 mL). The filtrate was washed with a solution of 5% aqueous hydrochloric acid (500 mL), water (1000 mL) followed by a solution of brine (1000 mL). The organic layer was concentrated under vacuum at 35° C./260-360 mm Hg to provide crude ethyl 3-cyclopropyl-2,2-difluoropropanoate (740 g), which was 79% pure by GC analysis. The crude product was then subjected to an oxidative work-up as described below to remove residual starting material (5% by area as determined by GC analysis).

The crude product (740 g) was dissolved in acetonitrile (370 mL), dichloromethane (370 mL) and water (555 mL) and then sodium metaperiodate (190 g) and ruthenium trichloride (0.465 g) were added to the solution with stirring at room temperature. The reaction was monitored by GC analysis and when all of the residual olefin was consumed (4-6 hours) the reaction was filtered and the organic layer was separated. The aqueous layer was extracted with dichloromethane (500 mL) and the combined organic layer was washed with aqueous sodium thiosulfate solution (3×1 L), saturated sodium bicarbonate solution (1×1.5 L) and brine (1.5 L) and dried over anhydrous sodium sulfate. The organic solvent was removed under reduced pressure and the resulting oil was distilled. The fraction distilling at 720 mm Hg, 60° C. gave ethyl 3-cyclopropyl-2,2-difluoropropanoate (318 g; 95% pure).

Example 3

Ethyl 3-cyclopropyl-2,2-difluoropropanoate

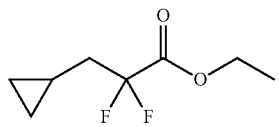

A solution of bromomethylcyclopropane (19.5 g, 0.144 mol) and 2-carboethoxy 1,3-dithiane (25.0 g, 0.130 mol) in dry N,N-dimethylformamide (55 mL) was added drop wise over 20 minutes to an ice cooled suspension of sodium hydride (60% oil dispersion, 6.24 g, 0.156 mol, 1.2 eq; pre-washed twice with n-pentane) in benzene (165 mL). The suspension was stirred at room temperature for 18 hours and then poured into 15% aqueous ammonium chloride. The mixture was extracted with methyl tert-butyl ether and the organic phase was separated, washed with water and then brine, dried over magnesium sulfate and filtered. The solvent was evaporated from the filtrate to give ethyl 2-(cyclopropylmethyl)-1,3-dithiane-2-carboxylate (31.2 g, 97.4%) as a light brown oil. $^1$H-NMR (400 MHz, CDCl$_3$): δ=0.07-0.15 (m, 2H), 0.37-0.47 (m, 2H), 0.76-0.89 (s, 1H), 1.25 (t, J=8 Hz, 3H), 1.70-1.85 (m, 1H), 1.88 (d, J=8 Hz, 2H), 2.01-2.13 (m, 1H), 2.54-2.65 (m, 2H), 3.13-3.26 (m, 2H), 4.19 (q, J=8 Hz, 2H).

A solution of ethyl 2-(cyclopropylmethyl)-1,3-dithiane-2-carboxylate (20.8 g, 0.084 mol) in acetone/water (97/3, v/v; 80 mL) was added drop wise over 30 minutes to a stirred suspension of N-bromosuccinimide in acetone/water (97/3, v/v, 1220 mL) at −5° C. The reaction mixture was stirred at the same temperature for 1 hour, while the progress of the reaction was monitored by thin layer chromatography, and then a mixture of methylene chloride/hexane (1/1, v/v, 500 mL) and aqueous sodium sulphite was added. The mixture was stirred until the colour faded from the organic layer. The phases were separated and the aqueous phase was extracted with methylene chloride/hexane (3×300 mL). The combined extracts were washed with aqueous sodium sulfite, water, aqueous sodium bicarbonate, brine and dried over magnesium sulfate. The solvent was removed under reduced pressure to afford ethyl 3-cyclopropyl-2-oxopropanoate (12.3 g, 93.4%), as a light yellow oil. $^1$H-NMR (400 MHz, CDCl$_3$): δ=0.13-0.21 (m, 2H), 0.54-0.65 (m, 2H), 0.97-1.10 (m, 1H), 1.38 (t, J=8 Hz, 3H), 2.72 (d, J=8 Hz, 2H), 4.33 (q, J=8 Hz, 2H).

A solution of bis(2-methoxyethyl)aminosulfur trifluoride in dry methylene chloride (50 mL) was added over 20 minutes to a solution of ethyl 3-cyclopropyl-2-oxopropanoate (12.3 g, 0.079 mol) in dry methylene chloride at −5° C., under nitrogen, and then ethanol (920 µl) was added as a catalyst. The reaction mixture was stirred at room temperature for 15 hours and then quenched with saturated aqueous sodium bicarbonate at 0° C. The mixture was extracted with methylene chloride after the evolution of carbon dioxide had ceased. The extract was washed with 10% aqueous sodium bicarbonate, water, dried over magnesium sulfate and filtered. The filtrate was concentrated under reduced pressure to yield ethyl 3-cyclopropyl-2,2-difluoropropanoate (11.6 g, 82.6%).

Example 4

3-Cyclopropyl-2,2-difluoropropan-1-ol

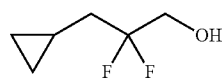

A solution of ethyl 3-cyclopropyl-2,2-difluoropropanoate (43.5 g, 0.244 mol), prepared as in Example 1, in absolute ethanol (100 mL) was added drop wise to a stirred slurry of sodium borohydride (9.45 g, 0.25 mol) in absolute ethanol (150 mL). The temperature of the mixture was allowed to rise to 35° C., whereupon cooling (ice/acetone bath) was applied and the temperature was maintained at 5° C. by controlling the rate of addition of the ester over 2 hours. The mixture then was stirred in an ice bath for 3 hours and then for 17 hours at room temperature. The reaction was quenched at 0° C. with 2M hydrochloric acid (180 mL) and the mixture was stirred for 30 minutes. The resulting homogenous mixture was poured into water (1000 mL) and extracted with diethyl ether (4×300 mL). The combined extracts were washed with 2M hydrochloric acid, water, 10% aqueous sodium bicarbonate and brine, dried over magnesium sulfate and filtered. The solvent was removed from the filtrate under reduced pressure. Distillation of the residue under reduced pressure gave 3-cyclopropyl-2,2-difluoro-1-propanol (28.3 g, 85% over 2 steps), as a colorless oil, b.p. 48-50° C./5 mbar. $^1$H-NMR (400 MHz, CDCl$_3$): δ=6:15-0.23 (m, 2H), 0.49-0.60 (m, 2H), 0.77-0.90 (m, 1H), 1.77 (bs, 1H), 1.80-1.90 (m, 2H), 3.83 (t, J=14 Hz, 2H); $^1$H-NMR (400 MHz, CD$_3$SOCD$_3$): δ=0.08-0.28 (m, 2H), 0.39-0.55 (m, 2H), 0.70-0.86 (m, 1H), 1.70-1.87 (m, 2H), 3.53-3.73 (m, 2H), 5.36 (t, J=4 Hz, 1H).

Example 5

Methyl 2-(benzhydrylimino)acetate

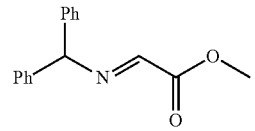

Benzhydrylamine (48.8 g, 0.266 mol) was added drop wise to a solution of glyoxylic acid methyl ester methyl hemiacetal (32 g, 0.266 mol) in methylene chloride (300 mL). The mixture was stirred for 3 hours at room temperature and then dried over magnesium sulfate. The mixture was filtered and the solvent was removed from the filtrate under reduced pressure to yield a viscous oil. Trituration with diisopropyl ether/heptane gave methyl 2-(benzhydrylimino)acetate (53.4 g, 79%) as an off white solid. $^1$H-NMR (400 MHz, CDCl$_3$): δ=3.82 (s, 3H), 7.17-7.31 (m, 10H), 7.73 (s, 1H).

Example 6 tert-Butyl 2-(diphenymethyleneamino)acetate

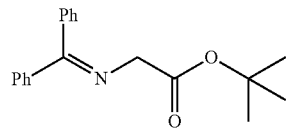

A solution of benzophenone imine (106.2 g; 587 mmol) and tert-butyl 2-aminoacetate hydrochloride (98.3 g; 587 mmol) in dichloromethane (1 L; HPLC grade) was stirred at ambient temperature for 20 hours. The reaction mixture was partitioned between dichloromethane (0.5 L) and water (1.5 L) and the layers were separated. The aqueous phase was extracted with dichloromethane (0.5 L) and the combined organic layers were dried (MgSO$_4$), filtered and concentrated in vacuo to give a slightly off-white solid. The resulting solid was triturated with n-hexane to give 141 g (83.1%) of the title product as a white solid. $^1$H-NMR (CDCl$_3$, 400 MHz) δ 7.62

(d, 2H, ArH), 7.21-7.42 (m, 6H, ArH), 7.13 (d, 2H, ArH), 4.05 (s, 2H, CH$_2$), 1.41 (s, 9H, C(CH$_3$)$_3$); $^{13}$C-NMR (CDCl$_3$, 100 MHz) δ 171.5, 169.8, 139.4, 136.2, 130.4, 128.8, 128.7, 128.6, 128.0, 127.7, 81.4, 56.3, 28.1.

Example 7

3-Cyclopropyl-2,2-difluoropropyl 1,1,2,2,3,3,4,4,4-nonafluorobutane-1-sulfonate

3-Cyclopropyl-2,2-difluoro-1-propanol (48.0 g 0.35 mol, 1 eq), prepared as in Example 4, was added to a 1 L jacketed vessel equipped with a mechanical stirrer, thermometer and gas inlet adapter. Dichloromethane (480 mL) and then triethylamine (42.7 g, 0.421 mol, 1.2 eq) was added. The reaction mixture was cooled to 0° C. and then perfluorobutane sulfonyl fluoride (127.9 g, 0.421 mol, 1 eq) was slowly added drop wise over 30 minutes maintaining a temperature of less than 5° C. The reaction was shown to be complete after one hour by thin layer chromatography (1:1/ethyl acetate:hexanes, silica, KMnO$_4$ dip). The mixture was concentrated under vacuum at 30° C. to provide a brown oil. Water (150 mL) was added and the product was extracted with methyl tert-butylether (250 mL). The organic layer was washed with water (2×150 mL), dried with anhydrous magnesium sulfate and filtered. The filtrate was evaporated under reduced pressure to provide 3-cyclopropyl-2,2-difluoropropyl 1,1,2,2,3,3,4,4,4-nonafluorobutane-1-sulfonate (140 g, 95% yield) as a brown oil. GC/MS: consistent with mass.

Example 8

Ethyl(R,S)-2-amino-5-cyclopropyl-4,4-difluoropentanoate hydrochloride

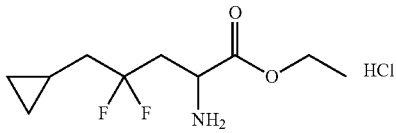

Ethyl 2-(diphenylmethyleneamino)acetate (72.95 g, 0.273 mol, 1 eq), obtained from commercial sources, was charged to a 2 L jacketed vessel equipped with a mechanical stirrer, thermometer and gas inlet adapter. Tetrahydrofuran (1260 mL) was added, followed by potassium tert-butoxide (33.7 g, 0.3 mol, 1.1 eq), and the reaction mixture stirred to give a deep yellow solution. The reaction was then cooled to 0° C., and 3-cyclopropyl-2,2-difluoropropyl 1,1,2,2,3,3,4,4,4-nonafluorobutane-1-sulfonate, prepared as in Example 7, (126 g, 0.3 mol, 1.1 eq) was added slowly maintaining a temperature of less than 5° C. (exotherm). The reaction was stirred at room temperature for 24 hours. HPLC analysis showed that the reaction was not complete. Additional 3-cyclopropyl-2,2-difluoropropyl 1,1,2,2,3,3,4,4,4-nonafluorobutane-1-sulfonate (12.0 g, 0.029 mol, 0.1 eq) and potassium tert-butoxide (3.0 g, 0.01 mol, 0.04 eq) were added and the mixture was stirred for 2 hours at room temperature. The pH of the mixture was adjusted to 2.5 with 25% sulfuric acid and the mixture was stirred until reaction was complete. The organic layer was separated and the tetrahydrofuran was removed under reduced pressure at 35° C. The resulting oil was re-dissolved in methyl tert-butyl ether and the solution was washed with water (2×100 mL). The solvent was removed under reduced pressure and hexanes (400 mL) were added to the residue. The solvent was removed at room temperature under reduced pressure and hexanes (400 mL) were added to the residue. The solvent was removed at room temperature under reduced pressure to provide an oil. The oil was taken up in dry methyl tert-butyl ether (400 mL) and hydrochloric acid gas (10 g, 1 eq) was added, resulting in precipitation of a white solid product, which was filtered off and dried at room temperature under reduced pressure to provide ethyl(R,S)-2-amino-5-cyclopropyl-4,4-difluoropentanoate hydrochloride (66.0 g, 94% yield). $^1$H NMR confirmed the desired structure.

Example 9

(R,S) Ethyl 2-(tert-butoxycarbonylamino)-5-cyclopropyl-4,4-difluoropentanoate

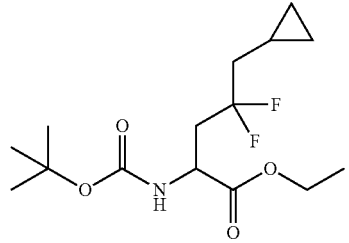

(R,S)-Ethyl 2-amino-5-cyclopropyl-4,4-difluoropentanoate hydrochloride (61.0 g, 0.237 mol, 1 eq), prepared as in Example 8, and di-tert-butyldicarbonate (46.55 g, 0.2133 mol, 0.9 eq) was added under nitrogen to a 1 L jacketed vessel, fitted with a mechanical stirrer and thermometer. Tetrahydrofuran (430 mL) was added and the reaction mixture was stirred to form a solution that was cooled to 10° C. Triethylamine (26.3 g, 0.26 mol, 1.1 eq) was slowly added drop wise, maintaining a temperature below 20° C. The reaction was complete after 2.5 hours by TLC (90:8:2/chloroform:methanol:acetic acid; 5% ninhydrin dip). The pH of the reaction mixture was adjusted to 3.5 by slow addition of 25% H$_2$SO$_4$ (30 mL). The organic layer was separated and the aqueous layer was extracted with methyl tert-butyl ether (3×50 mL). The organic layers were combined, dried over magnesium sulfate and concentrated under reduced pressure at 35° C. The residue was dissolved into methyl tert-butyl ether (300 mL) and water (100 mL) was added. The layers were separated and the organic phase was washed with 3% sulfuric acid (100 mL), water (2×100 mL) and 5% sodium bicarbonate (2×100 mL). The organic phase was dried over magnesium sulfate and concentrated under reduced pressure at 35° C. to obtain (R,S) ethyl 2-(tert-butoxycarbonylamino)-5-cyclopropyl-4,4-difluoropentanoate (55.3 g, 81% yield) as a yellow oil. The product was carried straight into the next step without further purification.

Example 10

(S)-2-(tert-Butoxycarbonylamino)-5-cyclopropyl-4,4-difluoropentanoic acid

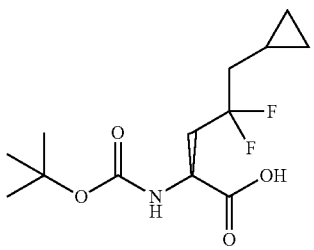

(R,S) Ethyl 2-(tert-butoxycarbonylamino)-5-cyclopropyl-4,4-difluoropentanoate (165 g, 0.514 mol, 1 eq), prepared as in Example 9, and sodium bicarbonate (21.6 g, 0.257 mol. 0.5 eq) were added to a 2 L round bottom flask fitted with a mechanical stirrer, a nitrogen inlet adapter and a thermometer. Acetone (660 mL) and water (742 mL) were added and the mixture was stirred while heated to 30° C. Alcalase 2.4 L (19.5 mL, 38 mL/mol) was added and the reaction was complete after 14 hours by HPLC to give a mixture of (R) ethyl 2-(tert-butoxycarbonylamino)-5-cyclopropyl-4,4-difluoropentanoate (49%) and (S) 2-(tert-butoxy carbonylamino)-5-cyclopropyl-4,4-difluoropentanoic acid (51%). The acetone was removed under reduced pressure at 35° C. Methyl tert-butyl ether (600 mL) was added and the layers separated. The organic layer was washed with water (150 mL) and the aqueous layer was washed with methyl tert-butyl ether (2×150 mL). Fresh methyl tert-butyl ether (500 mL) was added to the aqueous layer and the pH was adjusted to 2.1 using 25% sulfuric acid. The organic layer was separated and washed with water (2×300 mL). Crystallization was achieved by addition of heptanes (250 mL) at 50° C., followed by slow cooling to 5° C. The crystals were filtered and dried under reduced pressure at 35° C. for 24 hours to provide (S)-2-(tert-butoxycarbonylamino)-5-cyclopropyl-4,4-difluoropentanoic acid (75 g, 99%, 49% yield). Chiral HPLC analysis showed 100% optical purity.

Example 11

(S)-2-Amino-5-cyclopropyl-4,4-difluoropentanoic acid hydrochloride

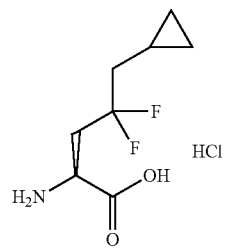

(S)-2-(tert-butoxycarbonylamino)-5-cyclopropyl-4,4-difluoropentanoic acid (75 g, 0.256 mol, 1 eq), prepared as in Example 10, was added to a 2 L round bottomed flask fitted with a mechanical stirrer, nitrogen inlet and thermometer. A mixture of hydrochloric acid (13.7 g, 0.375 mol, 1.5 eq) and acetonitrile (750 mL) and was added. White solids precipitated out during the reaction. After 2 hours the solids were filtered, washed with acetonitrile and dried in a vacuum oven at 30° C. for 24 hours to provide (S)-2-amino-5-cyclopropyl-4,4-difluoropentanoic acid hydrochloride (51 g, 87% yield). $^1$H NMR confirmed the desired structure.

Example 12

Methyl 2-amino-5-cyclopropyl-4,4-difluoropentanoate hydrochloride

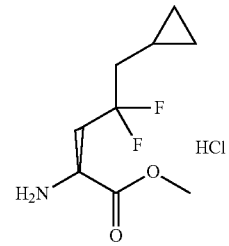

(S)-2-Amino-5-cyclopropyl-4,4-difluoropentanoic hydrochloride (51 g, 0.222 mol, 1 eq), prepared as in Example 11, was added to a 1 L jacketed vessel fitted with a mechanical stirrer, nitrogen inlet and a thermometer. Methanol (400 mL) was added and the mixture was stirred while thionyl chloride (52.9 g, 0.444 mol, 2 eqs) was slowly added dropwise over 30 minutes (exotherm). The reaction was heated to 45° C. for 18 hours. The solvent was removed under reduced pressure at 35° C. and methyl tert-butyl ether (200 mL) was added. The solvent was removed under reduced pressure and methyl tert-butyl ether (460 mL) was added. The mixture was stirred for 1 hour to form crystals. The crystals were filtered off, washed with methyl tert-butyl ether and dried in a vacuum oven at 35° C. for 24 hours to give methyl 2-amino-5-cyclopropyl-4,4-difluoropentanoate hydrochloride (53 g, 98% yield). $^1$H NMR confirmed the desired structure.

What is claimed is:

1. A process for the preparation of a (S)-alkyl 2-amino-5-cyclopropyl-4,4-difluoropentanoate hydrochloride of Formula 1:

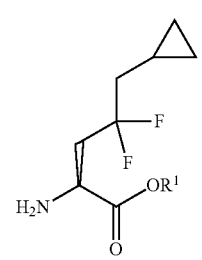

or salt thereof, where $R^1$ is a primary or secondary alkyl having 1 to 5 carbon atoms, which process comprises:

(a) selectively hydrolyzing a compound of Formula 2:

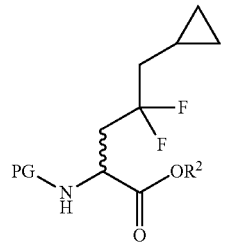

where PG is an amino protecting group and R² is alkyl, cycloalkyl, cycloalkylalkyl or arylalkyl, wherein any alkyl group comprising R² is a primary or secondary alkyl having 1 to 5 carbon atoms, to give a mixture of protected (R)-2-amino-5-cyclopropyl-4,4-difluoropentanoate and protected (S)-2-amino-5-cyclopropyl-4,4-difluoropentanoic acid;
(b) isolating the protected (S)-2-amino-5-cyclopropyl-4,4-difluoropentanoic acid;
(c) deprotecting the protected (S)-2-(amino)-5-cyclopropyl-4,4-difluoropentanoic acid to give (S)-2-amino-5-cyclopropyl-4,4-difluoropentanoic acid;
(d) treating the (S)-2-amino-5-cyclopropyl-4,4-difluoropentanoic acid with alcohol R¹OH;
(e) optionally converting the free base of the compound of Formula I to the acid addition salt.

2. The process of claim 1 for the preparation of (S)-methyl 2-amino-5-cyclopropyl-4,4-difluoropentanoate hydrochloride, which process comprises:
(a) reacting (R,S)-ethyl 2-(tert-butoxycarbonylamino)-5-cyclopropyl-4,4-difluoropentanoate with Alcalase to give a mixture of (R)-ethyl 2-(tert-butoxycarbonylamino)-5-cyclopropyl-4,4-difluoropentanoate and (S)-2-(tert-butoxycarbonylamino)-5-cyclopropyl-4,4-difluoropentanoic acid;
(b) isolating the (S)-2-(tert-butoxycarbonylamino)-5-cyclopropyl-4,4-difluoropentanoic acid;
(c) deprotecting the (S)-2-(tert-butoxycarbonylamino)-5-cyclopropyl-4,4-difluoropentanoic acid with hydrochloric acid to give S)-2-amino-5-cyclopropyl-4,4-difluoropentanoic acid hydrochloride; and
(d) treating the (S)-2-amino-5-cyclopropyl-4,4-difluoropentanoic acid hydrochloride with methanol.

3. A process for the preparation of a compound of Formula 2:

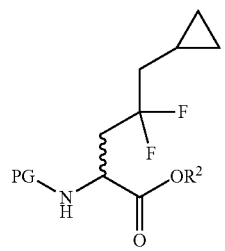

where PG is an amino protecting group and R² is alkyl, cycloalkyl, cycloalkylalkyl or arylalkyl, wherein any alkyl group comprising R² is a primary or secondary alkyl having 1 to 5 carbon atoms, which process comprises:

(a) condensing 3-cyclopropyl-2,2-difluoropropyl perfluoroalkane-1-sulfonate of Formula 4:

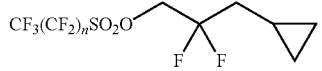

where n is 0, 1, 2, 3 or 4, with a 2-(diphenylmethyleneamino)acetate anion of Formula 3:

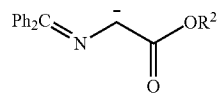

where R² is alkyl, cycloalkyl, cycloalkylalkyl or arylalkyl, wherein any alkyl group comprising R² is a primary or secondary at having 1 to 5 carbon atoms, to give the corresponding (R,S)-2-(diphenylmethyleneamino)-5-cyclopropyl-4,4-difluoropentanoate;
(b) hydrolyzing the (R,S)-2-(diphenylmethyleneamino)-5-cyclopropyl-4,4-difluoropentanoate with acid to give the corresponding (R,S)-2-amino-5-cyclopropyl-4,4-difluoropentanoate;
(c) optionally treating the (R,S)-2-amino-5-cyclopropyl-4,4-difluoropentanoate with acid to give the corresponding (R,S)-2-amino-5-cyclopropyl-4,4-difluoropentanoate acid addition salt; and
(d) treating the (R,S)-2-amino-5-cyclopropyl-4,4-difluoropentanoate or salt thereof with an amino protecting agent.

4. The process of claim 3 for the preparation of (R,S)-ethyl 2-(tert-butoxycarbonylamino)-5-cyclopropyl-4,4-difluoropentanoate, which process comprises:
(a) reacting 3-cyclopropyl-2,2-difluoropropyl 1,1,2,2,3,3,4,4,4-nonafluorobutane-1-sulfonate with (diphenylmethyleneamino)(ethoxycarbonyl)methanide to give ethyl (R,S)-2-(diphenylmethyleneamino)-5-cyclopropyl-4,4-difluoropentanoate;
(b) hydrolyzing the ethyl(R,S)-2-(diphenylmethyleneamino)-5-cyclopropyl-4,4-difluoropentanoate with acid to give ethyl(R,S)-2-amino-5-cyclopropyl-4,4-difluoropentanoate;
(c) treating the ethyl(R,S)-2-amino-5-cyclopropyl-4,4-difluoropentanoate with hydrochloric acid to give ethyl(R,S)-2-amino-5-cyclopropyl-4,4-difluoropentanoate hydrochloride; and
(d) treating the ethyl(R,S)-2-amino-5-cyclopropyl-4,4-difluoropentanoate hydrochloride with di-tert-butyldicarbonate.

5. A process for the preparation of the 3-cyclopropyl-2,2-difluoropropyl perfluoroalkane-1-sulfonate of Formula 4:

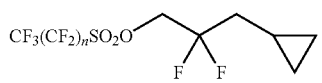

where n is 0, 1, 2, 3 or 4, which process comprises:
(a) reducing an alkyl 3-cyclopropyl-2,2-difluoropropanoate of Formula 5:

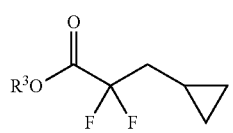

where R³ is hydrogen or alkyl having 1 to 5 carbon atoms, to give 3-cyclopropyl-2,2-difluoropropan-1-ol and
(b) reacting the 3-cyclopropyl-2,2-difluoropropan-1-ol with a perfluoroalkyl sulfonyl halide or a perfluoroalkyl sulfonic anhydride having the formula $CF_3(CF_2)_nSO_2X$ or $(CF_3(CF_2)_nSO_2)_2O$, respectively, where n is 0, 1, 2, 3 or 4 and X is chloro or fluoro.

6. The process of claim 5 for the preparation of 3-cyclopropyl-2,2-difluoropropyl 1,1,2,2,3,3,4,4-nonafluorobutane-1-sulfonate, which process comprises:
(a) reducing ethyl 3-cyclopropyl-2,2-difluoropropanoate to give 3-cyclopropyl-2,2-difluoropropan-1-ol and
(b) reacting the 3-cyclopropyl-2,2-difluoropropan-1-ol with perfluorobutane sulfonyl fluoride.

7. A compound of Formula 4:

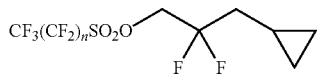

4 where n is 1, 2 or 3.

8. A process for the preparation of ethyl 3-cyclopropyl-2,2-difluoropropanoate, which process comprises reacting ethyl 2,2-difluoropent-4-enoate with diiodomethane in the presence of trifluoroacetic acid and diethylzinc or a zinc/copper couple.

9. The process of claim 8 where the reaction is carried out in the presence of trifluoroacetic acid and a zinc/copper couple.

10. A process for the preparation of ethyl 3-cyclopropyl-2,2-difluoropropanoate, which process comprises reacting the ethyl 3-cyclopropyl-2-oxopropanoate with a fluorinating agent.

11. The process of claim 10 where the fluorinating agent is bis(2-methoxyethyl)aminosulfur trifluoride.

* * * * *